(12) United States Patent
Tidrow et al.

(10) Patent No.: US 6,864,690 B1
(45) Date of Patent: Mar. 8, 2005

(54) APPARATUS FOR PRECISION MEASUREMENT OF MICROWAVE MATERIAL PROPERTIES AS FUNCTIONS OF TEMPERATURE AND FREQUENCY

(75) Inventors: Steven C. Tidrow, Silver Spring, MD (US); Daniel M. Potrepka, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 577 days.

(21) Appl. No.: 10/087,766

(22) Filed: Mar. 5, 2002

Related U.S. Application Data

(60) Provisional application No. 60/273,163, filed on Mar. 5, 2001.

(51) Int. Cl.[7] .............................................. G01R 27/04
(52) U.S. Cl. ....................................................... 324/636
(58) Field of Search ................................ 324/636, 637, 324/638–642, 76.11–76.19, 76.39, 646

(56) References Cited

U.S. PATENT DOCUMENTS 3,691,454 A * 9/1972 Hrubesh et al. ............ 324/316
4,255,702 A * 3/1981 Tricoles et al. ............. 324/637
6,605,949 B2 * 8/2003 Heidinger et al. .......... 324/636

OTHER PUBLICATIONS

"The Accurate Measurement of Permittivity by Means of an Open Resonator," A.L. Cullen and P.K. Yr, Proc. R. Soc. Lond. A. 325, 493–509 (1971).

* cited by examiner

Primary Examiner—N. Le
Assistant Examiner—Amy He
(74) Attorney, Agent, or Firm—William V. Adams

(57) ABSTRACT

Apparatus for the precise positioning of a sample of dielectric material into a cavity resonator system for obtaining dielectric constant, and other measurements. Precision micrometer drive units are provided to move the sample about a vertical axis, to tilt the sample, and to move the sample in X, Y and Z directions. The drive units are positioned on a bearing slide for ease of sample positioning into and out of the cavity. Selected drive units are controllable from a remote location so that the apparatus may be utilized in an environmental chamber whereby measurements may be accomplished without opening the chamber after each measurement. All components of the resonator system, positioning units, cables, etc. are chosen such that they are operable over the desired temperature range of operation.

9 Claims, 3 Drawing Sheets

APPARATUS FOR PRECISION MEASUREMENT OF MICROWAVE MATERIAL PROPERTIES AS FUNCTIONS OF TEMPERATURE AND FREQUENCY

CROSS-REFERENCE TO RELATED APPLICATIONS

The present application claims the benefit of priority of U.S. provisional patent application Ser. No. 60/273,163 filed on Mar. 5, 2001, which is hereby expressly incorporated by reference.

STATEMENT OF GOVERNMENT INTEREST

The invention described herein may be manufactured and used by or for the Government of the United States of America for government purposes without the payment of any royalties therefor.

BACKGROUND OF THE INVENTION

Accurate determination of microwave material permittivity and loss factor over the entire microwave regime and over the desired temperature range of operation are needed for accurate design, operation and evaluation of microwave components, circuits, antenna and systems. Microwave engineers can input such precise material parameters into currently available software programs to accurately model devices as functions of temperature. In this way, the number of iterations and time required to develop components, circuits, subsystems and systems that operate to the specified performance level and over the specified temperature range of operation can be reduced. Such efficient development, rather than development by trial and error, will lower component, circuit, subsystem and system cost.

Many methods have been devised for the accurate determination of microwave permittivity and loss factor, however, most of these methods employ cavity resonators or length of waveguide that are typically limited to measurement at one or only a few discrete frequencies and typically only one temperature, usually room temperature. Further, such methods typically become increasingly difficult to apply at higher frequencies and when evaluating high permittivity materials as the wavelength of radiation decreases. For solid dielectric materials a major problem is the accurate fabrication of a specimen to fit closely into the resonator or waveguide. Fabrication and measurement of ceramic samples can be especially difficult. Small air gaps between the dielectric and the metal resonator wall can cause large measurement errors with the magnitude of the error increasing with decreasing wavelength since the dimensions of the specimen are inversely proportional to the wavelength. At higher frequencies, it can be difficult to precisely determine the loss tangent of a material using the resonant cavity method if the sample's loss tangent is small. This occurs when the loss tangent falls below the reciprocal of the Q factor of the empty resonant cavity and occurs because Q factor varies as $f_o^{-3/2}$.

At the present time, due to the limits of typical resonant cavity methods, microwave engineers have limited information, typically data for only one temperature and a few discrete frequencies, about the dielectric constant and loss tangent of many technologically important microwave materials for use as input parameters for device design and development. Thus, it is important to develop versatile microwave methods that can be used to obtain comprehensive information of the dielectric constant and loss tangent of materials over a wide range of frequencies and temperatures. With such information, the microwave engineer will be able to more accurately and rapidly design and develop components, circuits, sub-systems and systems that meet performance specifications over the desired temperature range thus reducing cost.

An extremely powerful measurement method, known as the millimeter wave Fabry-Perot interferometer, for the determination of permittivity and loss factor has previously been demonstrated. An advantage of the confocal resonator or Fabry-Perot type interferometer is the ability to utilize the relatively high Q $TEM_{00p}$ modes for determination of permittivity and loss factor at numerous discrete frequency intervals which is dependent upon the plate separation distance and mode number as documented both theoretically and experimentally. The cavity is an open cavity resonator having opposed mirrors and a frame for holding a sample of the material, which is insertable into the cavity between the mirrors. The sample requires no electrical contacts and only needs to be placed uniformly in the beam. Microwave energy is transmitted via the mirrors, one to the other, and readings are taken, first without a sample and then with a sample, to obtain values of the desired properties.

Open confocal resonator cavities are commercially available; however, such systems have several severe limitations for precision determination of microwave permittivity and loss factor. The major drawbacks are (1) a fixed cavity length, L, that is preset by the manufacturer, (2) inadequately designed sample holder, and, (3) no ability for temperature variation. Because the resonant frequencies depend upon cavity length, a fixed cavity length limits the measurement frequencies to predetermined fixed discrete values. As discussed in more detail later, this problem is overcome by the present invention by placing the cavity resonator plates on micrometer drives that can be driven so as to vary the distance between the plates and hence the discrete resonant frequencies of the cavity.

The inadequately designed sample holder can be the source of relatively large errors and non-repeatability of measurements. This problem is overcome herein by placing the sample on an appropriately designed stage that allows precision sample alignment and repeatable sample insertion. The problem of the inability to vary temperature of the sample is also overcome by placing the whole instrument within an environmental chamber.

SUMMARY OF THE INVENTION

Apparatus according to the present invention includes an open cavity resonator, having opposed mirrors for obtaining data relative to a sample placed into the open cavity. The mirrors are supplied with microwave energy and provide analyzer equipment with microwave signals so that a determination of the sample's dielectric constant, and other parameters, may be made. A non-metallic sample holder, in the form of a ring, has a larger inner diameter than the outer diameter of confocal portion of either mirror. A plurality of precision micrometer drive units is provided enabling the sample to be initially and precisely positioned and to be precisely repositioned after a removal from the cavity. These drive units enable sample movement along the translation X, Y and Z axes as well as tilt movement and rotation movement about a vertical axis. The drive units are collectively moveable by virtue of their mounting on a bearing slide. Selected movement of the drive units are controllable from a remote location enabling the apparatus to be used within an environmental chamber so that measurements may be accomplished at various temperatures, without the requirement for opening the chamber after each measurement.

BRIEF DESCRIPTION OF THE DRAWINGS

The invention will be better understood, and further objects, features and advantages thereof will become more apparent from the following description of the preferred embodiment, taken in conjunction with the accompanying drawings, in which.

DETAILED DESCRIPTION OF THE PREFERRED EMBODIMENTS

Figure 1:
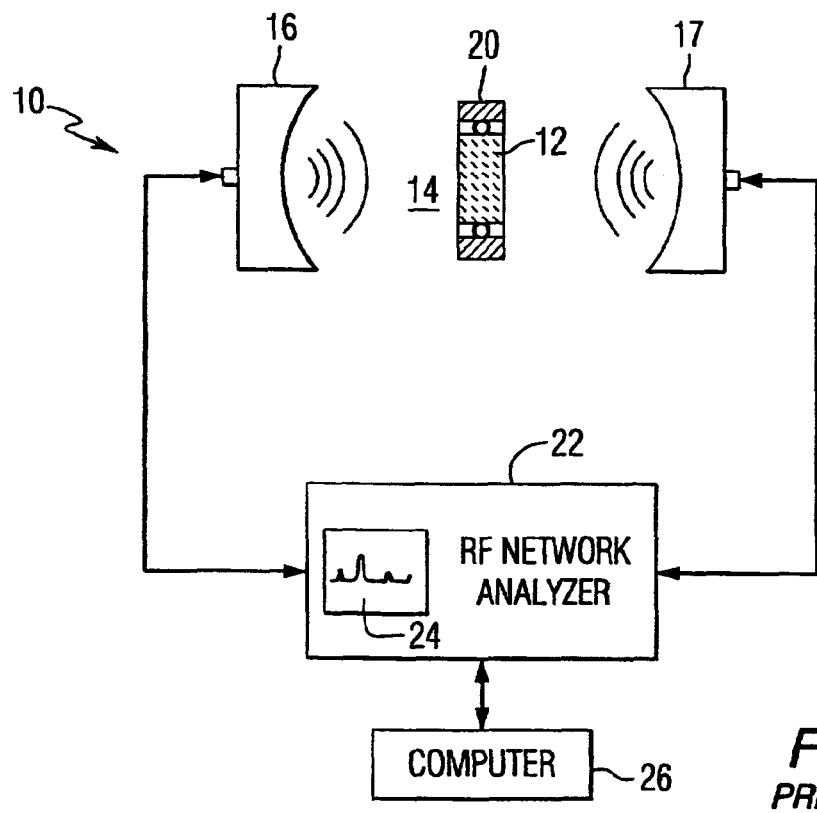
FIG. 1 is a block diagram of known apparatus for obtaining dielectric constant, and other measurements, with respect to a sample of material to be used in a microwave circuit.

In the drawings, which are not necessarily to scale, like or corresponding parts are denoted by like or corresponding reference numerals.

FIG. 1 illustrates typical apparatus 10 for obtaining dielectric constant, and other measurements, such as loss tangent, of a sample 12. The sample 12 is positioned in the cavity 14 between two confocal mirrors 16 and 17, and is maintained in position between the mirrors by means of a fixture in the form of a sample holder 20 with metal rods and screws, which are also disposed in the cavity 14. Both of the mirrors 16 and 17 are supplied with microwave signals from an RF network analyzer 22 having a screen 24. Some of the microwave energy is reflected back to the network analyzer 22 from the inputs to the mirrors, while the remainder of the energy is transmitted to the opposed mirror where it is reflected and maintained in the resonant cavity for a period of time and thereafter provided to the network analyzer 22. The network analyzer 22 is operative to extract data from the received signals and provides the information to a computer 26 having a program for determining the desired values of the parameters being measured.

In most instances multiple measurements are made, both with a sample in the resonant cavity 14 (loaded) and without the sample (unloaded), to obtain an average value with statistical errors for the parameters being measured. When making measurements on a sample, the operator performs a lengthy procedure for initializing the correct position, centering the uniform sample within the cavity. The apparatus of FIG. 1 however cannot be used to precisely insert the sample initially, and cannot reinsert the sample into the exact same position for multiple readings. In addition, if the sample holder 20 is a metal fixture it can generate objectionable eddy currents, that is, perturb the field, leading to possible errors in the measured values. Further, it is known that the value of dielectric properties may vary with temperature. The apparatus of FIG. 1 is not compatible for measuring the dielectric constant as a function of temperature because it is open to the environment and the cavity assembly must be made of materials capable of withstanding the temperature range of interest.

Figure 2:
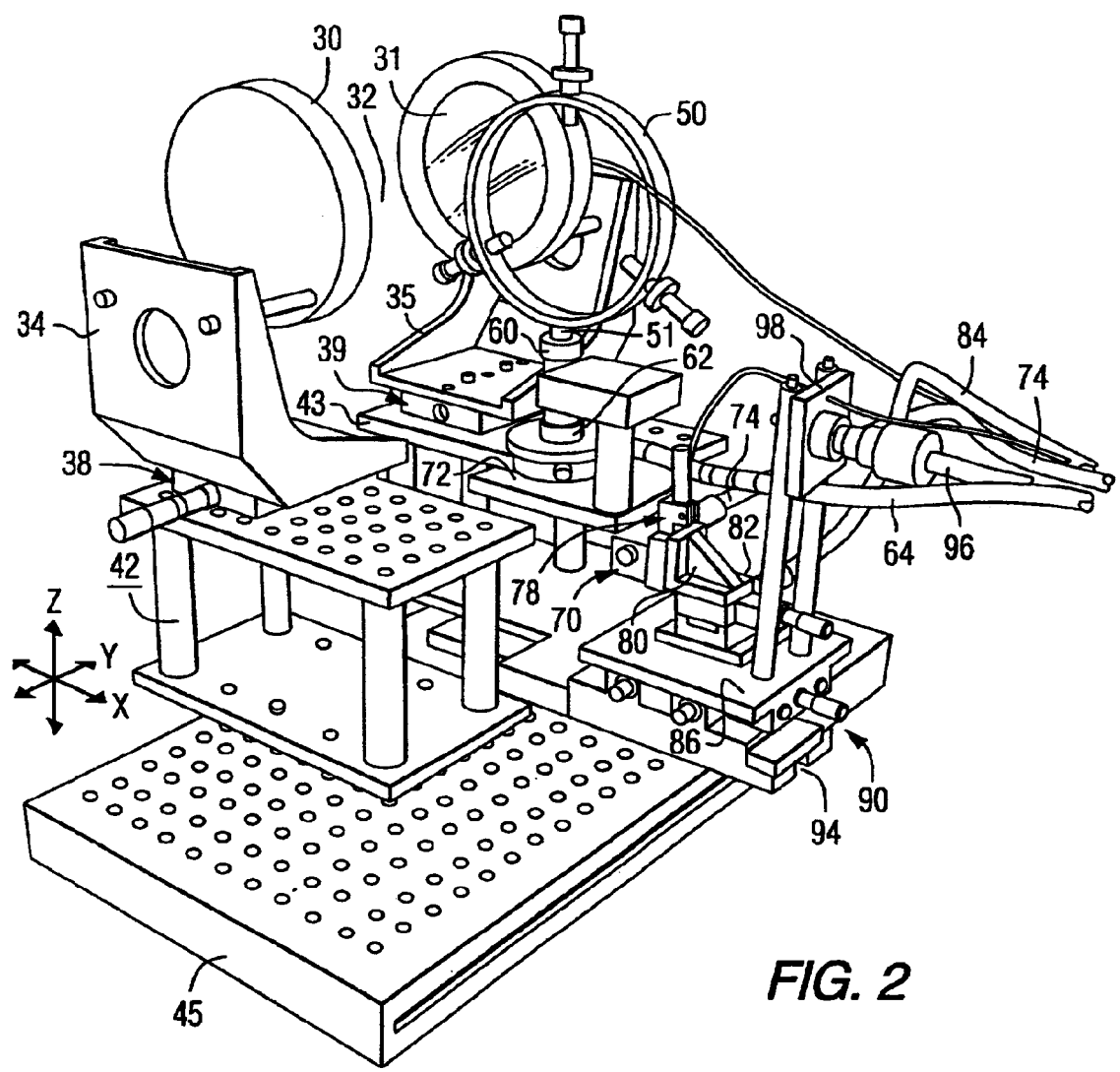
FIG. 2 illustrates one embodiment of the present invention.

FIG. 2 illustrates an embodiment of the present invention which obviates the drawbacks of the prior art measurement system. The improved apparatus of FIG. 2 includes opposed confocal mirrors 30 and 31 positioned on respective mounting brackets 34 and 35. The mirrors 30 and 31 are precisely moveable toward and away from one another, along a Y direction, by means of drive units 38 and 39, such drive units being constituted by micrometer drives which have an accuracy of around $1/10,000$ of an inch. These drive units are carried by respective platform stages 42 and 43 positioned on an optical bench 45. Alternatively but not shown in the figure, cables can be connected to drive units 38 and 39, so that the length of the cavity can be controlled via manipulation from a remote location.

Figure 3:
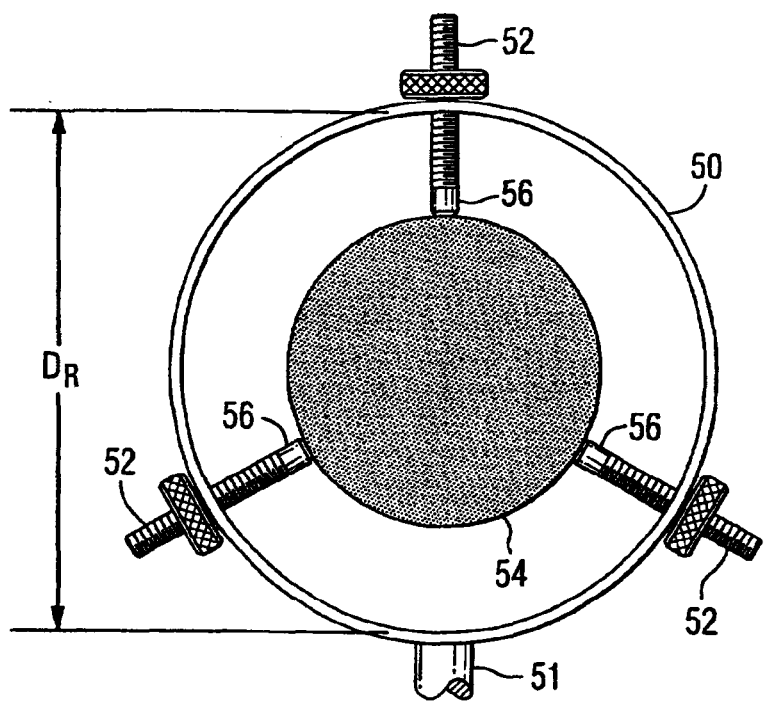
FIG. 3 is a view of an improved fixture for holding the sample under measurement.

A sample holder 50 is moveable into the cavity 32, along an X direction, for allowing a sample to be inserted and withdrawn from the cavity. With additional reference to FIG. 3, the sample holder 50 is in the form of a ring, supported by a shaft 51, and having an inside diameter DR, which is greater than the diameter DM of a confocal mirror 30 or 31. The holder is fabricated of a non-metallic material, such as plastic, so that no eddy currents are generated to interfere with the dielectric constant measurements. A series of adjustable metallic or non-metallic pins or screws 52 maintain a sample 54 in position for insertion into cavity 32, and if the sample is relatively small, the adjusting screws may be provided with non-metallic, for example teflon, extensions 56 of small diameter so as to limit the amount of non-essential material in the cavity that may cause perturbation errors.

Referring once again to FIG. 2, it is seen that the shaft 51 of holder 50 is inserted into, and held by, a cylinder 60, connected to a first drive unit 62. This first drive unit 62 is a precision micrometer drive which can rotate cylinder 60, resulting in the sample holder 50 being operably connected to the first drive unit 62 for rotation $\theta$ about a vertical axis. A cable 64 connected to drive unit 62, allows for precision control of $\theta$ from a remote location.

The holder 50 is operably connected to a second precision micrometer drive unit 70 via platform 72, for tilt movement $\phi$ about a tilt axis such that the top of the holder 50 will move toward one mirror more than the bottom of the holder. A cable 74 connected to drive unit 70, allows for precision control of $\phi$ from a remote location.

Vertical, or Z movement of the holder 50 is accomplished by its connection to a third precision micrometer drive unit 78, held by bracket 80, and connected to platform 72 via the second drive unit 70. The Z drive unit 78 is initially adjusted by hand and in general will not require subsequent adjustment.

A critical and sensitive positioning of the sample is in the Y direction, that is, toward and away from a mirror while the sample is in the cavity 32. Accordingly, a fourth precision micrometer drive unit 82 is provided and is operable from a remote location by means of cable 84. This Y drive unit 82 is mounted on a platform 86 and is coupled to bracket 80.

A fifth precision micrometer drive unit 90 is operable to move the bolder 50 in a horizontal X direction within the cavity 32 for fine-tuning the X position during initial setup. All of the above noted precision micrometer drive units, along with holder 50 are collectively moved into and out of cavity 32 by means of a precision bearing slide 94, moveable by means of a rod 96 connected to an extension bracket 98 secured to platform 86.

The positioning of the bearing slide is extremely accurate such that after a measurement is taken on a sample and it is withdrawn, the sample may be repositioned in the exact same location as the previous measurement, particularly if the sample is relatively thick. For thinner samples the drive units may have to be activated for precision sample placement. In most cases, only those drive units with remote operation capability will be used, that is drive unit 62 (θ), drive unit 70 (φ) and drive unit 82 (Y).

The remote operation capability is particularly useful when measurements are made under different temperature conditions. For example FIG. 4 conceptually illustrates the apparatus of FIG. 2 within an environmental chamber 100 having a temperature range of, for example, −50° C. to 100° C. Bearing slide 94, which carries all of the drive units, as well as the sample, may be moved to a desired position whereby the sample is precisely located within the cavity 32. After the measurement is made, the sample may be withdrawn from the cavity and subsequently reinserted to the exact same position. All of this movement is accomplished from outside of the chamber 100 by pushing or pulling the rod 96.

The rod 96 extends out of the chamber 100 through an insulated aperture 102 which may also accommodate the cables 64, 74 and 84 from respective drive units 62, 70 and 82. As indicated by dotted lines 104, 105 and 106, drive units 38, 39, 78 and 90 may also, if desired, be provided with remotely operated capabilities.

Figure 4:
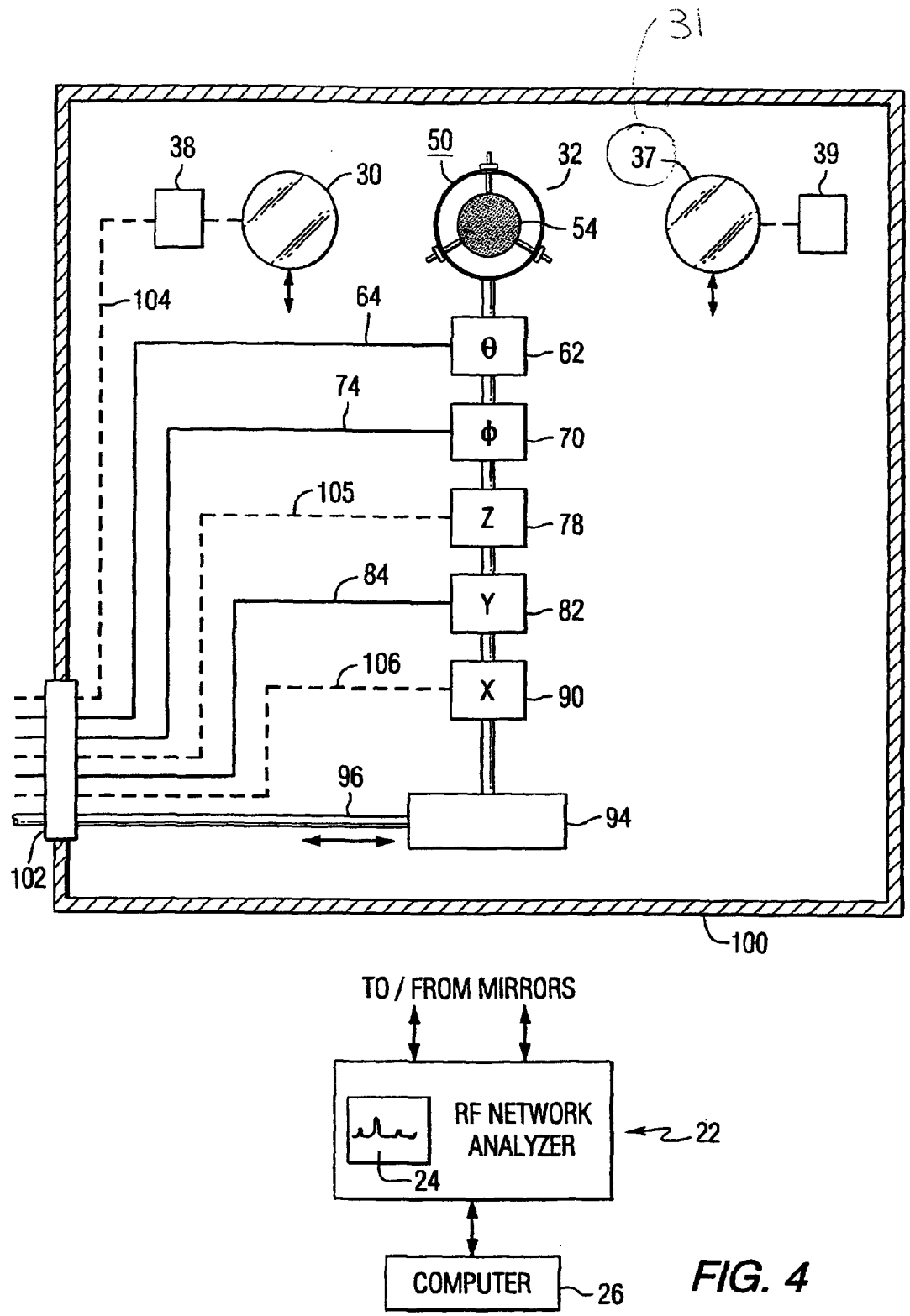
FIG. 4 is a block diagram illustrating certain features of the present invention.

With the arrangement of FIG. 4 the sample position can be initialized with facility and may be accurately repositioned after a reinsertion into the cavity, for tests at multiple temperatures. All of this is accomplished without the requirement to open the chamber after each measurement. Gross movement of the sample and drive units is accomplished by the rod 96 connected to bearing slide 94, while movement of selected drive units is accomplished by cables. Alternatively, such drive unit control may be by servo drives, suitably conditioned for low and high temperature operation.

It will be readily seen by one of ordinary skill in the art that the present invention fulfills all of the objects set forth herein. After reading the foregoing specification, one of a ordinary skill in the art will be able to effect various changes, substitutions of equivalents and various other aspects of the present invention as broadly disclosed herein. It is therefore intended that the protection granted hereon be limited only by the definition contained in the appended claims and equivalents. Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included

What is claimed is:

1. Apparatus for obtaining dielectric constant and other measurements of a sample, comprising:

an open cavity resonator having a pair of opposed confocal mirrors supplied with microwave energy, with each said mirror operable to provide corresponding microwave output signals for analysis for determination of said dielectric constant and other measurements;

a sample holder;

a first precision drive unit operably connected to said holder to rotate said holder, with said sample, about a vertical axis;

a second precision drive unit operably connected to said holder to tilt said holder, with said sample, relative to said mirrors;

a third precision drive unit operably connected to said holder to move said holder, with said sample, along a vertical axis;

a fourth precision drive unit operably connected to said holder to move said holder, with said sample, along a first horizontal axis toward and away from a said mirror;

a fifth precision drive unit operably connected to said holder to move said holder, with said sample, along a second horizontal axis when in said cavity of said resonator, said second horizontal axis being at a right angle with respect to said first horizontal axis;

a bearing slide;

said drive units being positioned on, and carried by said bearing slide which is moveable to position said holder into and out of said open cavity resonator.

2. Apparatus according to claim 1 wherein:

said sample holder is of a non-metallic material.

3. Apparatus according to claim 2 wherein:

said sample holder is of a plastic material.

4. Apparatus according to claim 1 wherein:

said sample holder is a ring.

5. Apparatus according to claim 4 wherein:

said confocal mirrors are circular and have a diameter $D_M$;

said ring has an inner diameter $D_R$; and wherein $D_R > D_M$.

6. Apparatus according to claim 1 wherein:

said apparatus is positioned within an environmental chamber for conducting measurements over a temperature range;

at least said first, second and fourth drive units and said bearing slide being controllable from outside of said chamber.

7. Apparatus according to claim 6 wherein:

said first, second and fourth drive units are controlled by respective cables which pass through an aperture in said chamber.

8. Apparatus according to claim 7 wherein:

said bearing slide is moveable by a rod which passes through said aperture.

9. Apparatus according to claim 1 wherein:

at least one of said mirrors includes a precision drive unit.

* * * * *